United States Patent [19]

Doyle

[11] Patent Number: 5,645,524

[45] Date of Patent: Jul. 8, 1997

[54] KNEE SUPPORT

[76] Inventor: Brian Peter Doyle, 390 Wellesly St. E, Toronto, Canada, M4X 1H6

[21] Appl. No.: 593,146

[22] Filed: Feb. 1, 1996

[51] Int. Cl.$^6$ .................................................. A61F 5/01
[52] U.S. Cl. .................................................. 602/16; 602/26
[58] Field of Search .................................. 602/5, 16, 23, 602/26; 623/27

[56] References Cited

U.S. PATENT DOCUMENTS

| 73,768 | 1/1868 | Allen | 602/16 |
|---|---|---|---|
| 4,323,059 | 4/1982 | Rambert et al. | 602/16 |
| 4,699,129 | 10/1987 | Aaserude et al. | 602/16 |
| 4,961,416 | 10/1990 | Moore et al. | 602/26 |
| 5,018,514 | 5/1991 | Grood et al. | 602/16 |
| 5,103,811 | 4/1992 | Crupi, Jr. | 602/16 |

*Primary Examiner*—Richard J. Apley
*Assistant Examiner*—David R. Risley

[57] ABSTRACT

A knee support for supporting an injured knee while permitting bending and straightening movements of such knee such movements involving both displacement of the femur portion of such joint away from the tibia portion and also involving sliding and tilting movement of such femur portion relative to such tibia portion, the knee support having an upper cuff which can be secured around a portion of a leg, above the knee, a lower cuff which can be secured around the leg below the knee, attachments on the upper and lower cuffs, and, linear bearings secured to the attachments on either side of the knee, the linear bearings enabling movement of one of the cuffs away from the other and enabling free displacement movement and sliding movement of the knee joint.

7 Claims, 3 Drawing Sheets

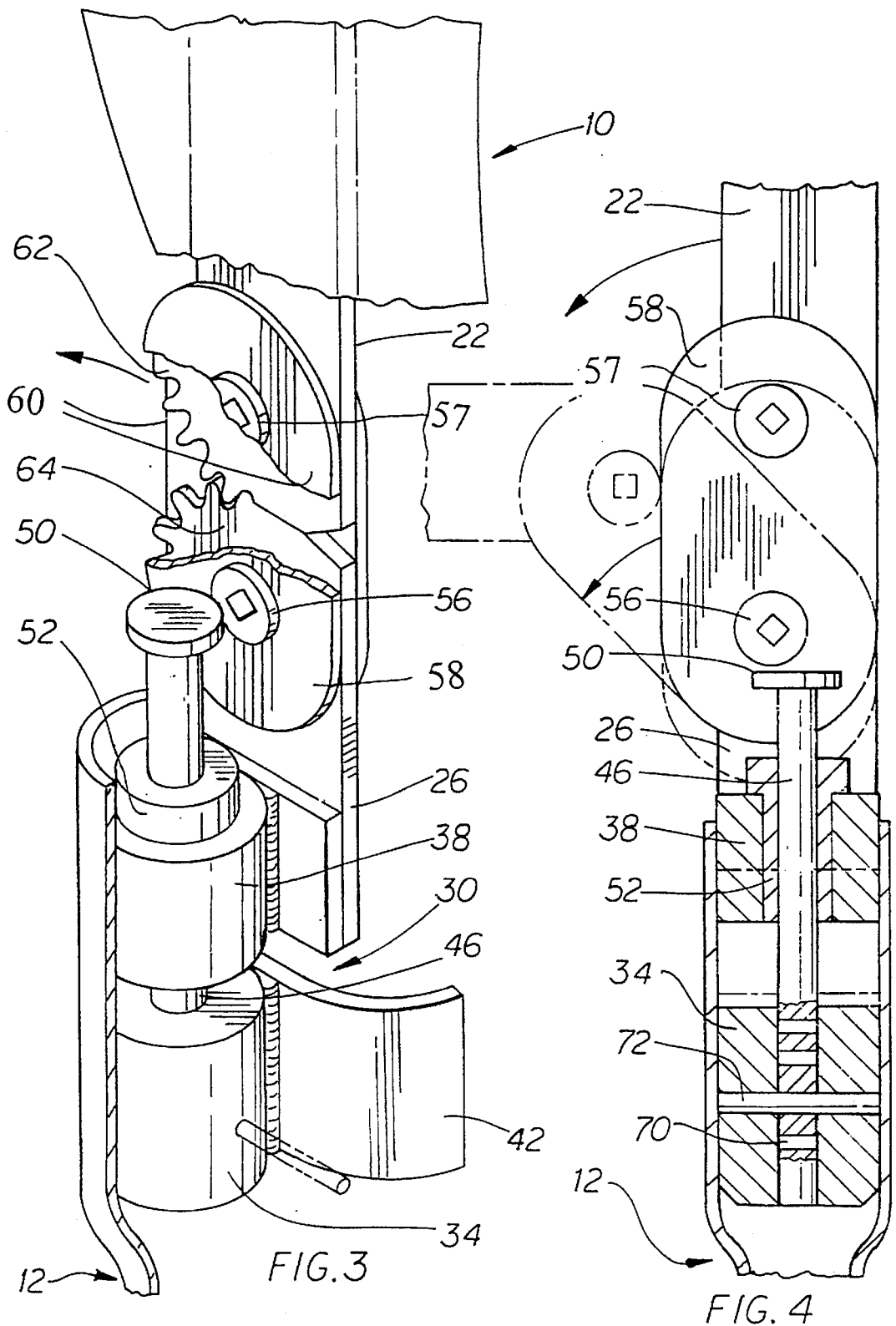

KNEE SUPPORT

FIELD OF THE INVENTION

The invention relates to a prosthesis, and in particular to a prosthesis designed to provide moveable support for the knee joint of the human body. Such prosthesis is usually known as a knee support.

BACKGROUND OF THE INVENTION

Injuries to the human knee joint are regrettably all too frequent, usually resulting from participation in some form of athletics, although of course they can arise in other ways. A healthy knee joint operates to provide forward and backward hinging motion of the lower leg (tibia) relative to the upper leg or thigh (femur), and also provides a certain degree of relative sliding motion, and a certain degree of tilting motion.

The knee joint consists basically of a large rounded knuckle, at the lower end of the femur, with a rearwardly directed radiussed portion, which terminates in a rearwardly directed rounded extension. The underside of the knuckle has a relatively large radiussed surface facing downwardly whereas the rearwardly directed extension has a shorter radius. The tibia in the lower leg has an enlarged upwardly directed surface. When the knee is straightened the larger radiussed portion of the femur rests directly on this upper end of the tibia.

However when the knee is hinged, the movement of the knee joint results a hinging action of the knuckle surface relative to the tibia, followed by a physical displacement of the femur knuckle relative to the tibia. In fact, a sliding action takes place between the two every time the knee is bent and straightened.

All of these complex movements, in a healthy knee joint, are controlled by a variety of ligaments connected to the bones and to muscle groups. When an injury occurs, one or more of these ligaments becomes either broken or separated from either its attachment to the bone or its attachment of the muscle group. In these cases, the knee is then substantially weaker, and can dislocate.

The basic facts surrounding knee injuries and the problems they cause are well known to the medical profession. Numerous attempts have been made to provide some form of prosthesis or knee support which can be attached to the leg above and below the knee, and which is provided with hinged joints allowing the knee to operate, under certain restrictions, and providing some support against movements which will tend to dislocate the knee. Generally speaking, however, these supports have been of relatively crude design. They are all based on the principle of an upper cuff to be strapped around the thigh, and a lower cuff to be strapped around the leg, and a pair of joint links extending between the lower and the upper cuffs on either side of the knee. Usually, the design provides for two double pivot link joints, one on each side of the knee brace, pivoting along two parallel axes, in an effort to simulate the actual movement of the knee.

In practise, however, these devices do not provide the function desired. When the knee is more or less straight or only slightly bent, then the average existing knee support provides a reasonable degree of support. However, as the knee bends progressively further, there is a hinging displacement which takes place in the knee joint and causes relative movement between the upper and lower leg. When this occurs, the standard knee support is incapable of conforming to such displacement. Instead, what happens is that the upper leg applies substantial pressure to the upper cuff, causing the upper cuff to become separated from the upper leg. When this occurs, the degree of support provided is substantially reduced. A more detailed explanation of the knee movements causing these problems will be given below.

A further problem in the design of standard knee supports is simply that of discomfort. When the knee is bent for any significant length of time for example, when driving a car, the pressure of the upper cuff on the thigh causes reduced blood circulation to the lower leg, and it is common for long distance drivers and truck drivers wearing such knee supports to in fact find that their lower leg and ankle and foot are completely numb after a long drive, and the joints swell up.

Eventually, the swelling of the joints become permanent.

A further problem caused by these standard knee supports is damage to the skin, especially of the upper leg. As the knee flexes and straightens out, there is a degree of relative movement between the upper leg and the upper cuff, setting up a rubbing action. It is in fact common for wearers of knee supports to use special pads and liners which fit between the knee support and the skin of the thigh. However, these only provide partial solutions to the problem. Where there is such relative movement on a frequent and constant basis, the problem of rubbing friction damaging the skin will always be there.

Finally, the design of the standard knee support, when it is worn properly and fitted tightly, provides significant restrictions on the movement of the knee, so that the knee cannot perform certain natural movements. In particular, the knee joint can no longer provide a twisting action and can no longer provide a sideways tilting action. Thus for example, a simple movement such as crossing the legs, becomes impossible for a person wearing a standard knee support which is fitted properly. Alternatively, if the knee brace is not tightly fitted to the leg, the dislocation of the knee can occur. Participation in many forms of athletics becomes impossible. Even running or jogging becomes impossible for many people wearing a standard knee support. The mere action of running causes a natural forward and backward translation movement between the two components of the knee joint, as will be described in detail below, which occur naturally in a healthy knee. However, this forward and backward translation simply cannot take place in an injured knee supported by the standard knee support, without there being some relative movement between the thigh and the upper cuff. In practise, a person jogging wearing a knee support on an injured knee finds that the upper cuff slops to and fro, allowing an opening to develop around the upper edge of the cuff. The fact that an opening has developed around the upper edge of the cuff is due to excessive pressure that has been caused by the back of the thigh against the back of the cuff. In other words, the thigh is trying to force the cuff to move in a way which is impossible for the cuff due to its crude design. What happens in effect during jogging, is that the upper cuff imposes an additional strain on the injured knee joint causing an improper translation of the two halves of the joint, so that when the person strides forward and lands on the injured leg, with the knee bent in the normal jogging position, the knee is already improperly stressed due to the standard knee support. The two portions of the knee joint at that moment are in fact displaced relative to one another into an unnatural position, and when the foot lands on the ground, extreme pain can be experienced in the supported knee. This pain results from the unusual stresses placed on the supported knee by the support itself. These stresses, as explained above, displace the upper knee joint relative to the lower knee joint into an improper position so that when the supported leg becomes the load bearing leg, the load is not transferred correctly from the upper leg to the lower leg.

In addition to the foregoing problems, many relatively simple leg movements were unsupported by the standard type of knee support. These included various movements in which the knee joint is subjected to a slight sideways tilt. This may be a simple movement such as crossing the legs when sitting in a chair, or it may happen in simple exercise programs, and relatively unstressful games such as tennis. In any of these situations where the injured knee was subjected to a sideways tilting movement or a sideways stress, the standard form of support did not provide support which was adequate, and dislocations of the already damaged knee joint were common.

A careful anatomical study of the problem has been made, starting with an examination of the actual movement of a healthy knee joint.

As generally described above, when the leg is straight, the lower larger radiussed surface of the femur joint rests on the flattened surface of the upwardly facing tibia joint supported by the lateral meniscus, and protected by the knee cap. The radius of curvature of the femur knuckle varies progressively from front to rear. The greater radius is on the forward portion, and the radius reduces on the rearward portion, so that when hinged onto the rearward portion the femur lifts slightly upwardly from the tibia. Thus, as soon as the knee is bent, a levering moment is set up by the rearward end of the femur, causing the femur to be displaced upwardly away from the tibia. Further movement causes rotation of the rounded smaller radiussed portion on the rearwardly directed free end of the femur joint, and a forward sliding movement of the knuckle along the surface of the tibia and the meniscus occurs, causing forward linear displacement of the femur relative to the tibia.

If such a knee joint is damaged, and is supported by a standard knee support, having a standard biaxial connecting link on either side, the initial levering moment of the femur joint relative to the tibia will attempt to draw the upper cuff of the support down along the surface of the thigh. Further bending of the knee, which causes rotation of the femur knuckle and sliding forward displacement, sets up considerable stresses on the underside of the upper cuff, usually where the upper cuff is strapped underneath the thigh, causing excessive pressure on the undersurface of the thigh. This in turn, will tend to lever the upper cuff away from the thigh, thereby losing virtually all support. Various designs of upper cuff have been proposed in an attempt to deal with this. Ideally the upper cuff should be of a fairly substantial design and of reasonable length to grasp a substantial portion of the upper thigh. However, the longer the upper cuff is made, the greater the problem. This is because a levering moment is set up between the strap, passing under the thigh, and the lower edge of the cuff which digs into the upper surface of the thigh. The longer the upper cuff is extended, the greater becomes the moment of this levering action. This causes undesired forward displacement of the femur joint knuckle along the surface of the tibia joint.

Attempts to overcome this have generally been directed to simply shortening or reshaping the upper cuff so that its engagement of the upper surface of the thigh was reduced in length, usually simply by cutting away a portion of the upper cuff, so as to relieve the pressure on the upper part of the thigh.

However, this simply still further reduced the support and did nothing to solve the problem.

It has now been recognised that the problems created by the vertical displacement of the femur, during initial movement, followed by lateral sliding displacement of the femur knuckle in the later knee movement, are not capable of being supported by the standard knee support. The standard knee support with its somewhat unscientific double axis biaxial joint had no means for accommodating a vertical displacement followed by a lateral transition of the knee joint. The standard knee support can simply accommodate a hinging movement forwardly and backwardly and nothing else. Since in fact the natural movement of the knee joint does not perform a simple hinging movement forward and backwardly, but moves in a much more complex way, then it is apparent that the standard knee support cannot provide adequate support for an injured knee.

The present invention, therefore, is directed to providing a knee support in which the joint action between the lower and upper cuff of the support is capable of conforming more precisely to the natural movement of the knee, and thus providing support for the injured knee over a much greater range of movement, and throughout various different types of movement, thereby enabling the wearer to take part in various normal activities such as sitting down, crossing the legs, driving a car and the like without inconvenience, and in fact enabling the wearer to take part in a number of athletic sports such as jogging, tennis, and the like, while being afforded a very considerable degree of improved support for the knee in a variety of different positions.

BRIEF SUMMARY OF THE INVENTION

With a view to satisfying as far as possible the foregoing problems of standard knee supports the invention comprises a knee support for supporting an injured knee while permitting bending and straightening movements of such knee such movements involving both displacement of the femur portion of such joint away from the tibia portion thereof and also involving sliding and tilting movement of such femur portion relative to such tibia portion, said knee support having an upper cuff adapted to be secured around a portion of a leg above the knee, a lower cuff adapted to be secured around said leg below said knee, attachment means on respective upper and lower cuffs adjacent either side of said knee, and, linear bearing means secured to said attachment means on either side of said knee, said linear bearing means being adapted to permit movement of one said cuff away from the other said cuff thereby enabling free hinging displacement movement of said knee displacement and a certain degree of tilting.

The invention also provides a knee support including swingable link means connected between said upper cuff and said linear bearing means on either side of said knee support.

The invention also provides a knee support wherein said link means comprises a link member, an upper pivot by which it attached to said upper cuff and a lower pivot by means of which it connected to said linear bearing means.

The invention also provides a knee support wherein said linear bearing means comprises a slidable rod member attached to one of said upper and lower cuffs, and a bearing body defining recess means therein for sliding reception of said slidable rod member, said bearing body being attached to the other of said upper and lower cuffs.

The invention also provides a knee support wherein said slidable rod member is attached to said lower cuff, and wherein said bearing body is attached to said upper cuff.

The invention also provides a linear bearing for such a prosthesis consisting of an elongated slide rod, fixed to the lower cuff, and a bearing body having a slide recess extending therethrough for receiving the slide rod, and in which the bearing body is attached to a portion of the link member connected to the upper cuff.

The invention also provides a link member which consists of an upper plate portion attached to the upper cuff, and a lower plate portion attached to the lower cuff, and a link member pivotally secured to the upper and to the lower link member, and gear means secured to said upper and to said lower plate portions and interengaged with one another so as to control relative movement therebetween.

The invention also provides adjustment means in said linear bearing for adjusting the length of linear movement available between said slide rod and said bearing body.

The various features of novelty which characterize the invention are pointed out with more particularity in the claims annexed to and forming a part of this disclosure. For a better understanding of the invention, its operating advantages and specific objects attained by its use, reference should be had to the accompanying drawings and descriptive matter in which there are illustrated and described preferred embodiments of the invention.

IN THE DRAWINGS

FIG. 3 is an enlarged perspective view of a portion of the knee support of FIG. 1 showing the knee straight;

FIG. 4 is a side elevational view, in section, corresponding to FIG. 3, illustrating a knee bent position;

Figure 5:
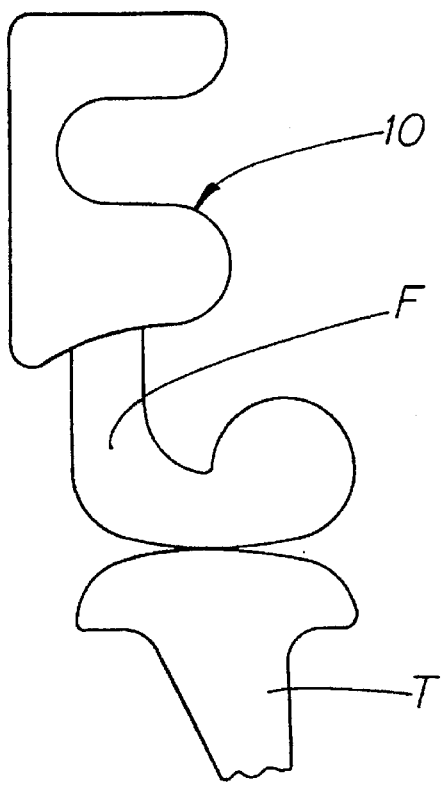
Figure 6:
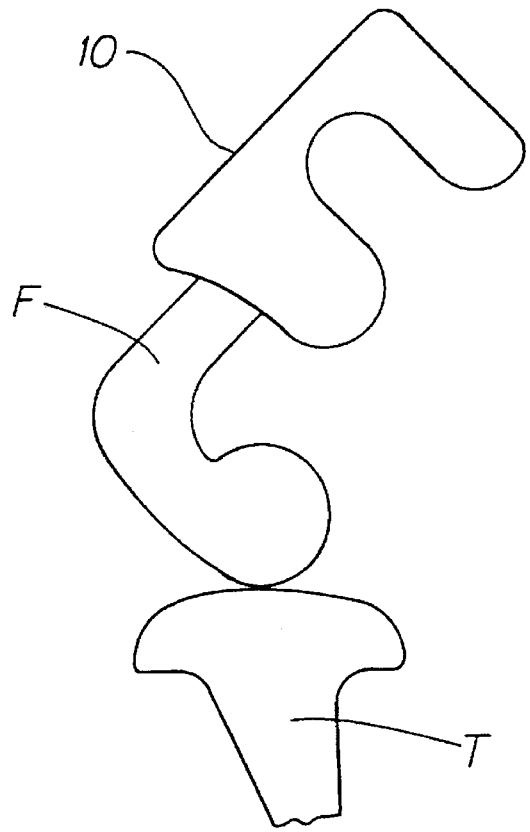
Figure 7:
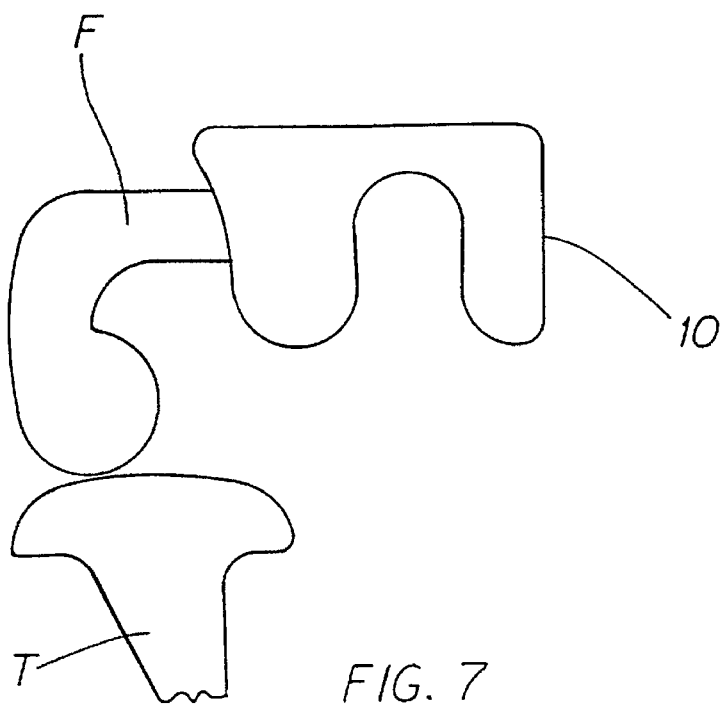

FIG. 5, 6, and 7, illustrate in schematic form, a knee joint, consisting of portions of the femur and the tibia, in positions corresponding to knee straight, knee partially bent, and knee fully bent.

DESCRIPTION OF A SPECIFIC EMBODIMENT

Figures 1, 2:
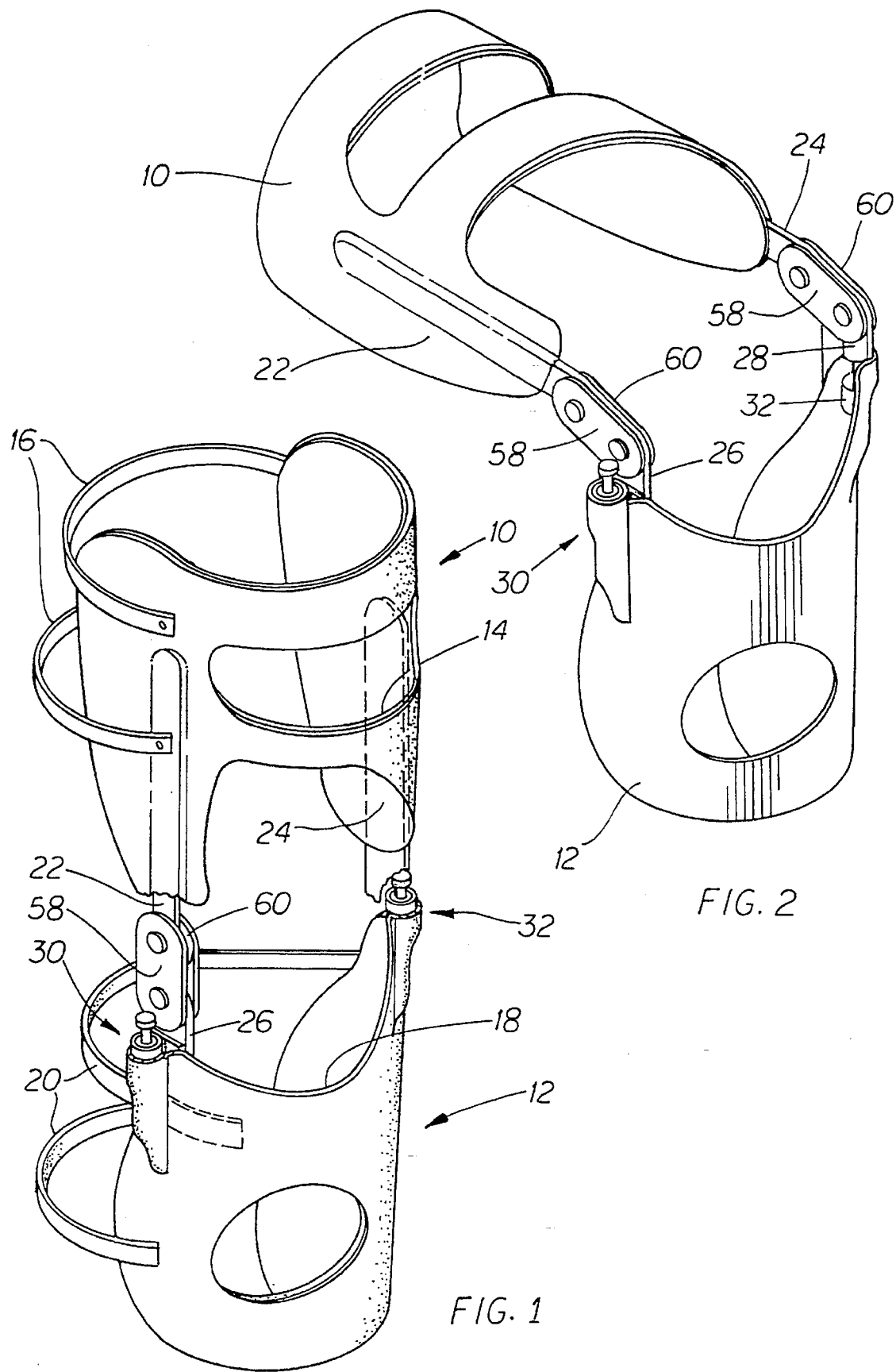
FIG. 1 is a perspective illustration in schematic form of a knee support illustrating the invention, with the knee straight.
FIG. 2 is a perspective view of the knee support of FIG. 1, shown in a position corresponding to the knee bent.

Referring first of all to FIG. 1, it will be seen that the knee support illustrated there for the purpose of explaining the invention, comprises an upper cuff 10, adapted to be strapped around the thigh, and a lower cuff 12 adapted to be strapped around the leg just below the knee. The upper cuff 10 consists of a semi rigid portion 14, typically made of synthetic plastic material, and having one or more flexible bands or straps 16, which may be wrapped around the underside of the thigh, and fastened by any suitable means such as buckles, hook and pile fastenings and the like.

The lower cuff 12 consists of a semi-rigid portion 18 having one or more flexible bands or straps 20 which may be wrapped around the back of the leg just below the knee. The strap(s) 20 are secured to one side of the cuff 12 and can be drawn tight and secured to the other side of the cuff by any suitable adjustable fastening means such as buckles, or hook and pile fastenings (not shown) such as are well known in the art. The shapes of the upper and lower cuffs 10 and 12 are selected to conform as far as possible to the shape of the thigh, and the lower leg respectively. They may be manufactured in various sizes to suit persons a various ages and muscle development. Such supports may be made up to suit individuals by selecting upper and lower cuffs of different shapes and sizes, and connecting them together in the manner described below.

In order to support the injured knee the upper and lower cuffs are movably connected together on either side of the knee. This is achieved by outer and inner upper attachment plates 22 and 24, and outer and inner lower connector plates 26 and 28. Upper plates 22–24 are secured by embedment in the respective sides of the upper cuff 10.

Connected with the respective lower connector plates 26–28 are respective linear bearing assemblies indicated generally as outer bearing assembly 30 and inner bearing assembly 32. The linear bearing assemblies comprise respective lower mounting blocks 34 and slide bearing bodies 38. The lower mounting blocks 34 are secured to respective embedment plates 42 by means such as by welding or braising. The lower mounting blocks 34 support elongated cylindrical slide rods 46. Rods 46 terminate at their upper ends in caps 50.

The slide bearing bodies 38 are formed with elongated bearing sleeves 52 therein, shaped and dimensioned to receive respective slide rods 46. The slide bodies 38–40 are secured eg. by welding or braising to connector plates 26–28. Plates 26–28 are pivotally connected eg. by rivets 56 to the lower ends of biaxial link plates 58 and 60. The upper ends of links 58,60 are pivotally connected by rivets 57 to respective upper attachment plates 22 and 24.

In this way the biaxial links or plates can permit rotational movement on two spaced apart parallel axes, in much the same way as the joints of the standard knee support. In addition, however, in accordance with the invention, the biaxial links 58,60 can also move upwardly and downwardly relative to the lower cuff and lower mounting blocks 34.

Upper gear segments 62 are formed on upper attachment plates 22–24 and lower gear segments 64 are formed on connector plates 26–28. The gear segments interengage to control hinging action of the links 58–60.

By this means when the injured knee bends causing linear displacement between the femur and the tibia the bearing bodies are able to slide upwardly on the bearing cylindrical rods. Further, when the knee bends still further between the femur and the tibia there is also a slight outward tilting motion of the femur relative to the tibia. When this occurs the linear bearing on the inside of the knee will be extended still further (i.e. the bearing body will slide further up it rod) and the linear bearing on the outside will retract slightly (ie the bearing body will slide down its rod) thereby accommodating the tilting movement of the knee joint.

It will thus be appreciated that by the use of the invention the knee is able to perform a much greater range of natural movements while still obtaining maximum support from the knee support. It will also be seen that the knee support is able to provide the range of support without imposing unusual stresses on the upper or lower leg. In fact such support is achieved without there being any tendency for the upper or lower cuff to move relative to the upper or lower leg. Thus by use of the knee support according to the invention there is improved comfort over a much greater range of knee movements without causing rubbing friction, skin irritation, or swelling of the leg, as was the case in standard knee supports.

If required, the range of movement permitted by the linear bearings can be adjusted. This can be achieved simply by extending, or by retracting, the length of one or both of the slide rods 46 out of, or into, their respective mounting blocks 34. This could be achieved in a number of ways such as threaded adjustment, but in this case is simply represented by a series of locating bores 70, formed transversely of each rod 46. The rods are secured in a desired position in blocks 34 by fastening pins 72. Repositioning of pins 72 will thus permit the rod(s) 46 to be secured in the desired positions.

FIGS. 5, 6, and 7, represent in schematic from the movements of the femur and tibia during bending of the knee.

The femur is shown as F and the tibia is shown as T. The various of smaller bones that complete the knee are omitted for the sake of clarity. It will be seen that when straight (FIG. 5) the flatter portion of the femur rests on the top of the tibia. As the knee starts to bend however the femur rolls back onto a rearward portion of reduced radius. This causes the femur to be displaced upwardly from the tibia (FIG. 6). As the knee bends further the femur tilts slightly relative to the tibia (FIG. 7). This explanation shows why the standard knee support cannot provide adequate support for the knee over a full range of movement.

The foregoing is a description of a preferred embodiment of the invention which is given here by way of example only. The invention is not to be taken as limited to any of the specific features as described, but comprehends all such variations thereof as come within the scope of the appended claims.

What is claimed is:

1. A knee support for supporting an injured knee while permitting bending and straightening movements of such knee, such movements involving both displacement of the femur portion of such joint away from the tibia portion thereof and also involving tilting movement of such femur portion relative to such tibia portion, said knee support comprising;

an upper cuff adapted to be secured around a portion of a leg, above said knee;

a lower cuff adapted to be secured around said leg below said knee;

upper attachment plate means secured on said upper cuff adjacent either side of said knee;

swingable link means connected to said upper attachment plate means on either side of said respective cuff, by first pivotal connection means;

lower attachment plate means secured to said swingable link means by second pivotal means adjacent either side of said knee;

linear bearing means movably connected to said lower attachment plate means and said lower cuff on either side of said knee, said linear bearing means being adapted to permit movement of one said cuff towards and away from the other said cuff, thereby enabling free movement of said knee both as to displacement and as to tilting as aforesaid.

2. A knee support as claimed in claim 1 wherein said swingable link means comprises two link plates.

3. A knee support as claimed in claim 1 wherein said linear bearing means comprises a fixed rod member attached to said lower cuff, and a bearing body defining recess means therein for sliding reception of said rod member, said bearing body being connected to said link means by said lower attachment plate means.

4. A knee support as claimed in claim 3 wherein said bearing body is operably connected by said swingable link means to said upper cuff, and is slidable relative to said rod member so as to permit relative movement between said upper and said lower cuff in response to bending movements of said knee.

5. A knee support as claimed in claim 4 including a mounting block attached by attachment means to said lower cuff, said rod member being mounted on said mounting block, and including an end cap on a free end of said rod member.

6. A knee support as claimed an claim 5 wherein said upper plate means attached to the upper cuff defines first gear means and wherein said lower attachment plate means defines second gear means, said first and second gear means meshing with one another.

7. A knee support as claimed in claim 5 including adjustment means in said linear bearing for adjusting the length of linear movement available between said rod member and said bearing body.

* * * * *